United States Patent
Frey et al.

(10) Patent No.: US 7,960,600 B2
(45) Date of Patent: Jun. 14, 2011

(54) PROCESS FOR IMPROVED META-XYLENE YIELD FROM $C_8$ AROMATICS

(75) Inventors: Stanley J. Frey, Palatine, IL (US); Jason T. Corradi, Arlington Heights, IL (US); Richard S. Kempf, Deerfield, IL (US); David W. Liu, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 56 days.

(21) Appl. No.: 12/622,824

(22) Filed: Nov. 20, 2009

(65) Prior Publication Data

US 2010/0305380 A1     Dec. 2, 2010

Related U.S. Application Data

(60) Provisional application No. 61/181,730, filed on May 28, 2009.

(51) Int. Cl.
*C07C 7/12*     (2006.01)
*C07C 7/04*     (2006.01)

(52) U.S. Cl. ......... 585/478; 585/820; 585/805; 585/828

(58) Field of Classification Search ................. None
See application file for complete search history.

(56) References Cited

U.S. PATENT DOCUMENTS

| | | | | |
|---|---|---|---|---|
| 2,763,604 A | * | 9/1956 | Dorsey et al. | 203/60 |
| 3,700,744 A | * | 10/1972 | Berger et al. | 585/478 |
| 3,773,846 A | | 11/1973 | Berger | |
| 4,306,107 A | | 12/1981 | Broughton | |
| 4,326,092 A | | 4/1982 | Neuzil | |
| 5,011,987 A | * | 4/1991 | Tokura et al. | 562/494 |
| 5,900,523 A | | 5/1999 | Kulprathipanja | |
| 2005/0038308 A1 | | 2/2005 | Wolff et al. | |
| 2007/0038012 A1 | | 2/2007 | Leflaive et al. | |
| 2008/0262282 A1 | | 10/2008 | Leflaive et al. | |
| 2008/0269535 A1 | | 10/2008 | Hotier et al. | |

* cited by examiner

*Primary Examiner* — Tam M Nguyen
(74) *Attorney, Agent, or Firm* — David J Piasecki

(57) ABSTRACT

Meta-xylene is recovered from admixture with other $C_8$ aromatic hydrocarbons including ortho-xylene by liquid phase adsorptive separation. Performance is improved by reducing the concentration of ortho-xylene through adding a sidecut to a prefractionator preparing the feedstock to adsorptive separation.

20 Claims, 2 Drawing Sheets

PROCESS FOR IMPROVED META-XYLENE YIELD FROM $C_8$ AROMATICS

CROSS-REFERENCE TO RELATED APPLICATION

This application claims the benefit of U.S. Provisional Application No. 61/181,730 filed May 28, 2009.

FIELD OF THE INVENTION

This invention relates to the production of xylene isomers from an aromatics mixture. More specifically, the invention relates to adsorptive separation of meta-xylene from a mixture of $C_8$ aromatics including other xylenes and ethylbenzene.

BACKGROUND OF THE INVENTION

The xylene isomers are important intermediates which find wide and varied application in chemical syntheses. Para-xylene is a feedstock for terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

A typical $C_8$-aromatics stream containing all of the xylene isomers and ethylbenzene is not readily separated into individual components due to their close boiling points. Ortho-xylene often is separated by fractional distillation, but requires a tower usually having 100-150 trays with high reflux ratios. Ethylbenzene can be separated by superfractionation with even more difficulty, but this generally is impractical. Para-xylene/meta-xylene separation by distillation is commercially impossible. Para-xylene has been separated by crystallization for some time, and adsorptive separation as disclosed in U.S. Pat. No. 2,985,589 has advanced to dominate commercial production.

Meta-xylene adsorptive separation, as disclosed in U.S. Pat. No. 3,773,846, U.S. Pat. No. 4,306,107, U.S. Pat. No. 4,326,092 and U.S. Pat. No. 5,900,523, also has been applied commercially. One issue in commercialization is that the presence of a significant concentration of ortho-xylene in the feed to meta-xylene adsorptive separation significantly increases equipment sizes and utility costs. This is not a problem if ortho-xylene is recovered by fractionation, but is important if the usual concentration of ortho-xylene is present in the feedstock to meta-xylene recovery.

BRIEF SUMMARY OF THE INVENTION

The object of the invention is to mitigate the high capital and utility costs associated with a significant concentration of ortho-xylene in a feed mixture to a process for meta-xylene recovery by adsorption.

A broad embodiment of the invention is a process for recovering high-purity meta-xylene from a feedstock comprising $C_8$ and heavier aromatic hydrocarbons which comprises (a) distilling the feedstock to separate $C_8$ aromatic hydrocarbons from heavier hydrocarbons in a xylene column which comprises a sidecut for obtaining an ortho-xylene concentrate; and, (b) contacting the $C_8$ aromatic hydrocarbons in a selective-adsorption step at liquid-phase adsorption conditions with an adsorbent comprising a zeolite, adsorbing the meta-xylene, removing the nonadsorbed portion of said mixture from contact with said adsorbent by means of a raffinate stream and recovering the high-purity meta-xylene by desorption with a desorbent at desorption conditions.

A more specific embodiment is a process for recovering high-purity meta-xylene from an unextracted feedstock comprising $C_8$ and heavier aromatic hydrocarbons which comprises (a) distilling the feedstock to separate $C_8$ aromatic hydrocarbons from heavier hydrocarbons in a xylene column which comprises a sidecut for obtaining an ortho-xylene concentrate; and, (b) contacting the $C_8$ aromatic hydrocarbons in a selective-adsorption step at liquid-phase adsorption conditions with an adsorbent comprising a zeolite, adsorbing the meta-xylene, removing the nonadsorbed portion of said mixture from contact with said adsorbent by means of a raffinate stream and recovering the high-purity meta-xylene by desorption with a desorbent at desorption conditions.

A yet more specific embodiment is a process for recovering high-purity meta-xylene from a feedstock comprising $C_8$ and heavier aromatic hydrocarbons which comprises (a) distilling the feedstock to separate $C_8$ aromatic hydrocarbons from heavier hydrocarbons in a xylene column which comprises a sidecut for obtaining an ortho-xylene concentrate;

(b) contacting the $C_8$ aromatic hydrocarbons in a selective-adsorption step at liquid-phase adsorption conditions with an adsorbent comprising a zeolite, adsorbing the meta-xylene, removing the nonadsorbed portion of said mixture from contact with said adsorbent by means of a raffinate stream and recovering the high-purity meta-xylene by desorption with a desorbent at desorption conditions; and, (c) isomerizing the raffinate stream with an isomerization catalyst at isomerization conditions to obtain an isomerized stream and distilling the isomerized stream along with the feedstock to separate $C_8$ aromatic hydrocarbons from the heavier hydrocarbons and an ortho-xylene concentrate.

DETAILED DESCRIPTION OF THE INVENTION

The feedstock to the present invention comprises $C_8$ and heavier aromatic hydrocarbons, and the heavier aromatics should be substantially removed before processing the $C_8$ aromatics to recover meta-xylene. The $C_8$ aromatics generally will have an ethylbenzene content in the broad range of about 1 to 50 wt-%, a para-xylene content in the range of 0 to 30 wt-%, a meta-xylene content in the broad range of 20 to 95 wt-% and an ortho-xylene content in the range of 1 to 35 wt-%. If derived from the reforming of petroleum naphtha, more usual ranges are from about 5 to 20 wt-% ethylbenzene, about 10 to 25 wt-% para-xylene, about 35 to 55 wt-% meta-xylene and 15 to 30 wt-% ortho-xylene.

The feedstock may be derived from any of a variety of original sources, e.g., petroleum refining, thermal or catalytic cracking of hydrocarbons, coking of coal, or petrochemical conversions. Preferably the feedstock to the present invention is found in appropriate fractions from various petroleum-refinery streams, e.g., as individual components or as fractions obtained by the selective fractionation and distillation of catalytically cracked or reformed hydrocarbons. The feedstock need not comprise highly-concentrated aromatics; the process of this invention allows the recovery of meta-xylene from streams such as catalytic reformate with or without subsequent aromatics extraction to obtain an extracted feedstock. A nonextracted feedstock to the present process may contain nonaromatic hydrocarbons, i.e., naphthenes and paraffins, in an amount up to 30 wt-%, but preferably comprises at least about 95 wt-% aromatics.

The present process can be applied in any recovery process in which one of the compounds in the feed interferes with the recovery of a desired product. It could be applied, for example, to the recovery of either para-xylene or meta-xylene based on either a fractional crystallization process or an adsorptive separation process, both of which are well known in the art. It is within the scope of the invention that both para-xylene and meta-xylene are recovered from a $C_8$-aromatics mixture. The invention is detailed herein with respect to its preferred application to the adsorptive separation of meta-xylene.

Figure 1:
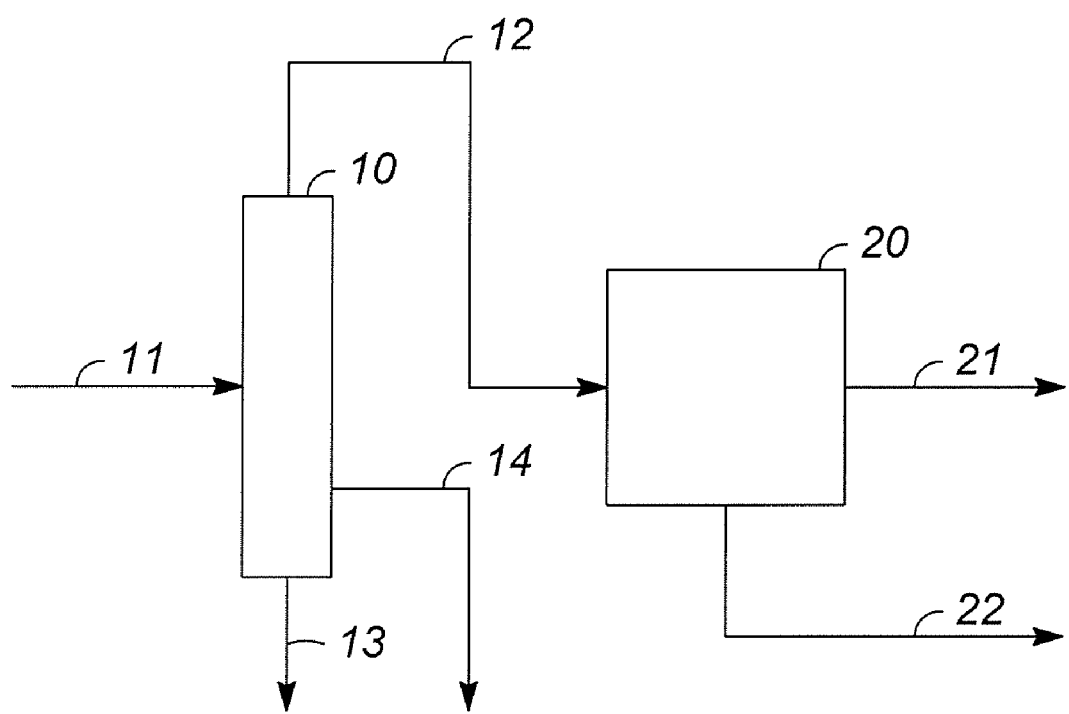
FIG. 1 illustrates the meta-xylene recovery process of the invention.

The feedstock is fractionated, as shown in FIG. 1, to remove $C_9$ and heavier compounds boiling above $C_8$ aromatics. Column 10 processes feedstock 11 to recover $C_8$ aromatics overhead in stream 12. Preferably the stream 12 feedstock to adsorption contains limited amounts (less than 5 mole %, preferably less than 2 mole %) of other compounds, such as $C_9$ aromatics, and more preferably is essentially 100% $C_8$ aromatics. The heavy materials are removed from the bottom of the column in stream 13.

Stream 14 represents an ortho-xylene concentrate taken as a sidecut from column 10. The sidecut contains at least about 40 wt-%, more usually at least about 50 wt-%, and especially at least about 60 wt-%, ortho-xylene. By removing the ortho-xylene as a sidecut prior to extracting meta-xylene from the $C_8$ aromatics, the feed concentration of the key component in the adsorptive separation with meta-xylene during extraction is reduced. Ortho-xylene optionally may be recovered from this stream by fractionation.

The $C_8$ aromatics in stream 12 are processed in meta-xylene extraction 20 in a selective-adsorption step. High-purity meta-xylene, preferably having a purity of at least 99 wt-%, is recovered in stream 21 over an adsorbent which selectively adsorbs the m-xylene, and stream 22 contains the remaining nonadsorbed $C_8$ aromatics as raffinate.

Any of the conventional apparatus employed in static bed fluid-solid contacting may be used for the selective adsorption. A moving-bed flow system suitable for use in the process of the present invention is the cocurrent high efficiency simulated moving bed process disclosed in U.S. Pat. No. 4,402,832 and U.S. Pat. No. 4,478,721, incorporated by reference herein. Countercurrent moving-bed or simulated-moving-bed countercurrent-flow systems are highly preferred for commercial installations. In a simulated moving bed process, the adsorption and desorption operations are continuously taking place, which allows both continuous production of an extract and a raffinate stream and the continual use of feed and desorbent streams. The operating principles and step sequence of a moving bed flow system are described in U.S. Pat. No. 2,985,589; U.S. Pat. No. 3,310,486; and, U.S. Pat. No. 4,385,993, incorporated herein by reference herein for their teaching in this regard. In such a system, it is the progressive movement of multiple liquid access points down an adsorbent chamber that simulates the upward movement of adsorbent contained in one or more chambers. Coincident with this simulated upward movement of the solid adsorbent is the movement of the liquid occupying the void volume of the packed bed of adsorbent. To maintain the simulated movement, a liquid flow down the adsorbent chamber may be provided by a pump. As an active liquid access point moves through a cycle, that is, from the top of the chamber to the bottom, the chamber circulation pump provides different flow rates. A programmed flow controller may be provided to set and regulate these flow rates.

Terms used herein are defined as follows. The "extract" is meta-xylene (stream 21) which is more selectively adsorbed by the adsorbent. A "raffinate" is a compound or type of compound that is less selectively adsorbed (stream 22, other xylenes and ethylbenzene). The term "desorbent" is a material capable of desorbing an extract component from the adsorbent.

A liquid-phase operation is preferred for the selective-adsorption process because of the nature of the materials being separated. Adsorption conditions can include a temperature range of from about 20° to about 200° C., with a range of 100° to about 150° C. being preferred and a temperature of about 120° to about 130° C. being highly preferred. Adsorption conditions also include a pressure range of from about atmospheric to about 3.5 MPa as required to insure liquid phase operations with pressures from about atmospheric to about 1.8 MPa being preferred. Desorption conditions preferably include the same temperature and pressure as used for adsorption.

The desorbent used in selective adsorption primarily must displace an extract component from the adsorbent with reasonable mass flow rates without itself being so strongly adsorbed as to unduly prevent being displaced in an adsorption cycle. Secondly, desorbent materials must be compatible with the particular adsorbent and the particular feed mixture. Additionally, desorbent materials must not chemically react with or cause a chemical reaction of either an extract component or a raffinate component.

Since both the raffinate and the extract from adsorption typically contain desorbent materials, desorbent materials should additionally be substances which are easily separable from the feed mixture that is passed into the process. At least a portion of the desorbent material is normally recovered from the extract and the raffinate streams of an adsorptive separation process by distillation or evaporation and returned to the selective adsorption.

The adsorbent used in the selective adsorption comprises a zeolite, suitably an X or Y zeolite. The adsorbent preferably comprises a sodium Y zeolite, generally described in U.S. Pat. No. 3,130,007. It is preferred that a minor portion of the sodium ions are replaced by lithium ions. Typically, the adsorbent particles used in separation processes contain small zeolite crystals dispersed in an amorphous inorganic matrix such as alumina or clay. A clay binder comprising both silica and alumina is preferred. The zeolite will ordinarily be present in the adsorbent particles in amounts ranging from about 75 to about 98 wt. %.

Figure 2:
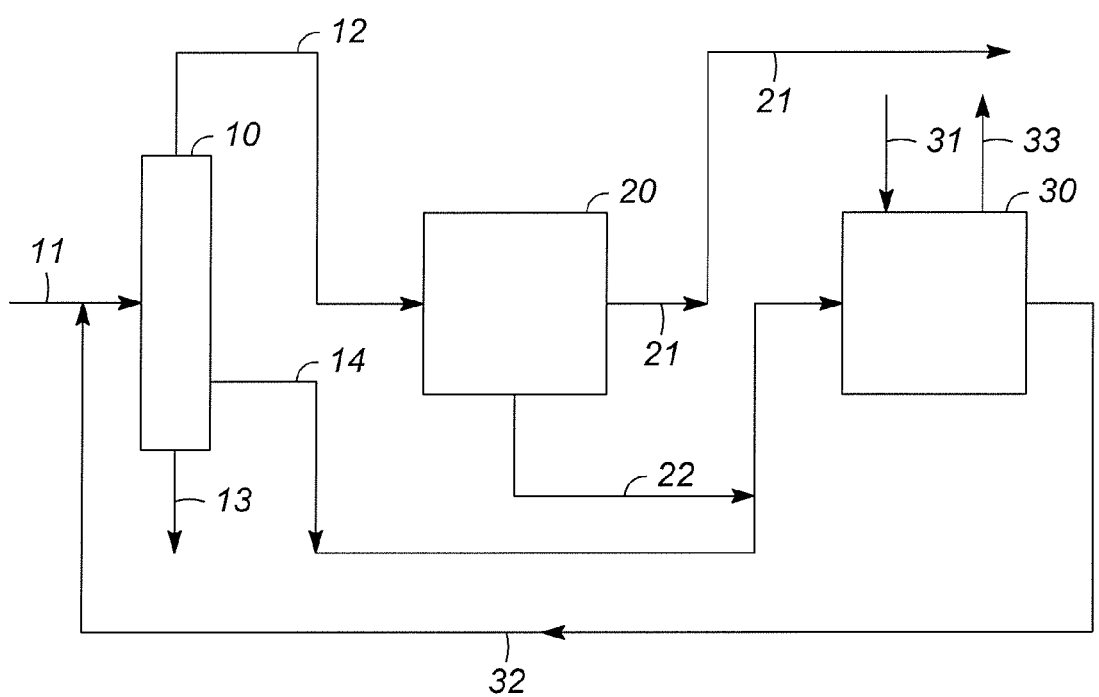
FIG. 2 illustrates meta-xylene recovery with the addition of $C_8$-aromatics isomerization to increase meta-xylene yield.

FIG. 2 adds isomerization of $C_8$ aromatics from which meta-xylene has been recovered as described above for the flowscheme of FIG. 1. Following meta-xylene recovery per FIG. 1, raffinate stream 22 passes to isomerization unit 30 preferably along with ortho-xylene concentrate 14 and optionally along with hydrogen in stream 31. The isomerization establishes a near-equilibrium distribution of $C_8$ aromatics, thus increasing the concentration of meta-xylene in stream 32. Any ethylbenzene in the raffinate is either converted to additional xylenes or converted to benzene by dealkylation, depending upon the type of isomerization catalyst used. Light ends, notably toluene and lighter compounds, are removed in stream 33; such removal may be combined with other operations in an aromatics complex. The isomerized product may be sent to xylene column 10 to remove heavy materials and an ortho-xylene concentrate as shown or, alternatively, sent directly to meta-xylene extraction unit 20.

The raffinate stream is contacted in isomerization unit 30 with an isomerization catalyst at isomerization conditions. The isomerization catalyst typically comprises a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a non-zeolitic molecular sieve. The zeolitic aluminosilicate (or zeolite) component typically is either a pentasil zeolite, which include the structures of MFI, MEL, MTW, MTT and FER (IUPAC Commission on Zeolite Nomenclature), a beta zeolite, or a mordenite. The non-zeolitic molecular sieve typically is one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992). The metal component typically is a noble metal component, and may include an optional base metal modifier component in addition to the noble metal or in place of the noble metal. The noble metal is a platinum-group metal selected from one or more of platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the isomerization catalyst range from about 0.01 to about 10 wt-%, with the range from about 0.1 to about 3 wt-% preferred. Suitable zeolite amounts in the catalyst range from about 1 to about 99 wt-%, preferably between about 10 to about 90 wt-%, and more preferably between about 25 to about 75 wt-%. The balance of the catalyst comprises an inorganic oxide binder, typically alumina. One isomerization catalyst for use in the present invention is disclosed in U.S. Pat. No. 4,899,012, which is hereby incorporated by reference.

Typical isomerization conditions include a temperature in the range from about 0° to about 600° C. and pressure from atmospheric to about 5 MPa. The liquid hourly hydrocarbon space velocity of the feedstock relative to the volume of catalyst is from about 0.1 to about 30 $hr^{-1}$. The hydrocarbon contacts the catalyst in admixture with a gaseous hydrogen-containing stream in a line at a hydrogen-to-hydrocarbon mole ratio of from about 0.5:1 to 15:1 or more, and preferably a ratio of from about 0.5 to 10. If liquid phase conditions are used for isomerization, then no hydrogen is added to the unit.

The examples shown below are intended to further illustrate the process of this invention and should not be construed as limiting the scope and spirit of said process. The examples present test results for various adsorbents and conditions determined using the previously described dynamic pulse and reverse pulse test methods corroborated and adjusted to match actual commercial results.

Example

A $C_8$- and heavier aromatic feedstock was evaluated for meta-xylene recovery according to the methods of the known art and the method of the invention. The feedstock had the following composition in wt-%:

| | |
|---|---|
| $C_7$ nonaromatics | 0.059 |
| Toluene | 0.095 |
| $C_8$ nonaromatics | 0.819 |
| Ethylbenzene | 14.838 |
| Para-xylene | 10.144 |
| Meta-xylene | 26.837 |
| Ortho-xylene | 14.957 |
| $C_9$ nonaromatics | 0.541 |
| $C_9$+ aromatics | 31.710 |

Yields and operating factors were calculated for conventional meta-xylene extraction and isomerization and for the process of the invention with a xylene-column sidecut comprising an ortho-xylene concentrate; the figures were normalized to a standard of 100 for the conventional scheme.

| | Conventional | Invention |
|---|---|---|
| C8-Aromatics Feedstock | 100 | 100 |
| Meta-Xylene Product | 100 | 100 |
| Adsorptive Separation Feed Rate | 100 | 94 |
| Adsorptive Separation Desorb. Circulation | 100 | 94 |
| Isomerization Unit Feed Rate | 100 | 107 |
| Xylene Column Feed Rate | 100 | 104 |

Relative utility costs were calculated on a typical basis in order to compare the invention to the known art with results as follows per metric ton of meta-xylene; the process of the invention results in substantial savings:

| Relative utility cost/ton metaxylene | Conventional | Invention |
|---|---|---|
| Adsorptive Separation | 0.828 | 0.778 |
| Isomerization Unit | 0.066 | 0.071 |
| Xylene Column | 0.106 | 0.110 |
| Total | 1.000 | 0.959 |

The invention claimed is:

1. A process for recovering high-purity meta-xylene from a feedstock comprising $C_8$ and heavier aromatic hydrocarbons which comprises:
    (a) distilling the feedstock to separate $C_8$ aromatic hydrocarbons from heavier hydrocarbons in a xylene column which comprises a sidecut for obtaining an ortho-xylene concentrate;
    (b) contacting the $C_8$ aromatic hydrocarbons in a selective-adsorption step at liquid-phase adsorption conditions with an adsorbent comprising a zeolite, adsorbing the meta-xylene, removing the nonadsorbed portion of said mixture from contact with said adsorbent by means of a raffinate stream and recovering the high-purity meta-xylene by desorption with a desorbent at desorption conditions.

2. The process of claim 1 wherein the ortho-xylene concentrate comprises at least about 40 wt-% ortho-xylene.

3. The process of claim 1 further comprising fractionation of the ortho-xylene concentrate to recover high-purity ortho-xylene.

4. The process of claim 1 wherein the adsorbent comprises Y-zeolite.

5. The process of claim 1 wherein the desorbent consists essentially of toluene.

6. The process of claim 1 wherein the desorbent consists essentially of indane.

7. The process of claim 1 wherein the adsorption conditions include a temperature of from 100 to 150° C.

8. The process of claim 1 further comprising recovering paraxylene from the feedstock.

9. The process of claim 1 wherein the feedstock has been prepared by extraction of aromatics from a hydrocarbon mixture.

10. A process for recovering high-purity meta-xylene from a feedstock comprising $C_8$ and heavier aromatic hydrocarbons which comprises:
  (a) distilling the feedstock to separate $C_8$ aromatic hydrocarbons from heavier hydrocarbons in a xylene column which comprises a sidecut for obtaining an ortho-xylene concentrate;
  (b) contacting the $C_8$ aromatic hydrocarbons in a selective-adsorption step at liquid-phase adsorption conditions with an adsorbent comprising a zeolite, adsorbing the meta-xylene, removing the nonadsorbed portion of said mixture from contact with said adsorbent by means of a raffinate stream and recovering the high-purity meta-xylene by desorption with a desorbent at desorption conditions; and,
  (c) isomerizing the raffinate stream with an isomerization catalyst at isomerization conditions to obtain an isomerized stream and distilling the isomerized stream along with the feedstock to separate $C_8$ aromatic hydrocarbons from the heavier hydrocarbons and an ortho-xylene concentrate.

11. The process of claim 10 wherein the ortho-xylene concentrate comprises at least about 40 wt-% ortho-xylene.

12. The process of claim 10 further comprising fractionation of the ortho-xylene concentrate to recover high-purity ortho-xylene.

13. The process of claim 10 wherein the adsorbent comprises Y-zeolite.

14. The process of claim 10 wherein the desorbent consists essentially of toluene.

15. The process of claim 10 wherein the desorbent consists essentially of indane.

16. The process of claim 10 wherein the adsorption conditions include a temperature of from 100 to 150° C.

17. The process of claim 10 further comprising recovering paraxylene from the feedstock.

18. The process of claim 10 wherein the feedstock has been prepared by extraction of aromatics from a hydrocarbon mixture.

19. The process of claim 10 wherein the feedstock is unextracted.

20. The process of claim 1 wherein the feedstock is unextracted.

* * * * *